(12) United States Patent
Sistrunk

(10) Patent No.: US 12,220,372 B2
(45) Date of Patent: Feb. 11, 2025

(54) VIBRATING AND HEATING MASSAGE VEST

(71) Applicant: Mark Lamar Sistrunk, Oakwood Village, OH (US)

(72) Inventor: Mark Lamar Sistrunk, Oakwood Village, OH (US)

( * ) Notice: Subject to any disclaimer, the term of this patent is extended or adjusted under 35 U.S.C. 154(b) by 584 days.

(21) Appl. No.: 17/521,751

(22) Filed: Nov. 8, 2021

(65) Prior Publication Data

US 2022/0142854 A1    May 12, 2022

Related U.S. Application Data

(60) Provisional application No. 63/110,684, filed on Nov. 6, 2020.

(51) Int. Cl.
    *A61H 23/02*    (2006.01)

(52) U.S. Cl.
    CPC ..... *A61H 23/02* (2013.01); *A61H 2201/0207* (2013.01); *A61H 2201/165* (2013.01); *A61H 2201/5025* (2013.01); *A61H 2201/5035* (2013.01); *A61H 2201/5043* (2013.01); *A61H 2205/04* (2013.01); *A61H 2205/062* (2013.01); *A61H 2205/081* (2013.01)

(58) Field of Classification Search
    CPC .... A41D 1/02; A41D 1/03; A61H 2201/0221; A61H 2201/0228; A61H 2201/0235; A61H 2201/0285; A61H 2201/0207; A61F 7/00
    See application file for complete search history.

(56) References Cited

U.S. PATENT DOCUMENTS

| | | | | |
|---|---|---|---|---|
| 6,120,468 A | * | 9/2000 | Tseng | A61H 23/0254 601/57 |
| 6,329,639 B1 | * | 12/2001 | Akutsu | H05B 3/0095 219/549 |
| 7,207,953 B1 | * | 4/2007 | Goicaj | A61H 23/02 601/134 |
| 2007/0197941 A1 | * | 8/2007 | Koen | A61H 7/001 601/79 |
| 2020/0188224 A1 | * | 6/2020 | Mountjoy | A61H 1/00 |
| 2022/0331198 A1 | * | 10/2022 | Dietrich | A61H 23/02 |

FOREIGN PATENT DOCUMENTS

| | | | | |
|---|---|---|---|---|
| CN | 114681291 A | * | 7/2022 | A61F 7/007 |
| TW | 201424721 A | * | 7/2014 | A61H 9/0007 |

* cited by examiner

*Primary Examiner* — Kendra D Carter
*Assistant Examiner* — Jaeick Jang

(57) ABSTRACT

A unique and innovative vest provides vibrating and heating massage. A controller is used to control vibrating modules and heating elements positioned on the vest. Through a vibration button and a heat button, the controller allows a user to selectively control vibrating and vibrating/heating massages. Using increase/decrease intensity buttons the vest facilitates optimal massage effects per the user's desire. The vibrating modules is configured to vibrate and/or oscillate in various controlled directional and rotational movements, providing a therapeutic massage. Multiple body zone switches corresponding to various massage zones of the user's body offer the user efficient control of any specific local area for achieving effective massage, thus substantially facilitating the recovery of muscles/tissues injury, alleviation of body pain, stress relief of neck, back, shoulders, etc. Further, the massage vest includes a design that promotes good posture while the user is seated.

19 Claims, 10 Drawing Sheets

VIBRATING AND HEATING MASSAGE VEST

The current application claims a priority to the U.S. Provisional Patent application Ser. No. 63/110,684 filed on Nov. 6, 2020. The current application is filed on Nov. 8, 2021, while Nov. 6, 2021 was on a weekend.

FIELD OF THE INVENTION

The present invention generally relates to a massage device. More specifically, the present invention relates to a massage vest that can be conveniently worn with a snug fit by a user and greatly improving the user's health at the same time by massaging and warming up the user's neck, back, shoulders, etc.

BACKGROUND OF THE INVENTION

A convenient massage vest is in demand. Various companies have developed vests that perform massages. Generally, massage vests, when worn and operated, promote blood circulation by massaging various parts of the upper body of a user, including the neck, shoulders, and back of the upper body of the user.

Many existing massage vests include controllers that are configured to control the speed, local massage functions, and temperature. However, these vests are bulky and/or heavy, and generally, do not include an appealing design because most of the vests focus primarily on massage functionality only.

Other existing massage vests are not properly designed to provide effective massage to the neck and back of the user. For example, many vests do not allow sufficient contact with the user's body, especially on the lower back, to provide effective massage. In addition, most of the massage vests available on the market are not convenient for the user to carry during travel because of their design, and some are not equipped with proper power connection mechanisms such as USB (Universal Serial Bus) or electrical car plugs in a way that the user can wear the vest and use it in moving vehicles, including automobiles, planes, bicycles, motorized scooters, etc. Further, most existing wearable car massagers are expensive and rarely provide a good fit to the user, often shifting or loosening with use, and are difficult to carry when traveling. Thus, there is a need to develop a device to solve the problems.

The present invention is intended to address the aforementioned problems associated with and/or otherwise improve on conventional devices through an innovative massage vest device that is designed to offer a convenient and effective means to provide massage to the user without compromising an appealing design while incorporating other problem-solving features.

SUMMARY OF THE INVENTION

The present invention offers a unique and innovative vest to a user, which provides vibrating and heating massage. The vest uses a controller to control a plurality of vibrating modules and a plurality of heating elements that are positioned on the vest. Through a power switch, a vibration button, and a heat button, the controller allows the user to selectively control vibrating massage and vibrating/heating massage. Additionally, the controller provides the intensity control of the vibration and heating through increase/decrease intensity buttons that further facilitate optimal massage effects per the user's desire. The massage vibrating modules may be positioned on the vest for massaging various areas on the back, neck, and shoulders of the user. The massage vibrating modules may be configured to vibrate and/or oscillate in various controlled directional and rotational movements, providing a therapeutic massage to the user. Multiple body zone switches corresponding to various massage zones of the user's body offer the user efficient control of any specific local area for achieving effective massage, thus substantially facilitating the recovery of muscles/tissues, alleviation of body pain, injury, stress relief of neck, back, shoulders, etc. The massage vest can use alternating current (AC) and direct current (DC) power sources which include batteries, car adaptors, USB (universal serial bus) power plugs, etc.

Further, the massage vest of the present invention includes a design that promotes good posture while the user is seated. Additionally, the massage vest includes adjustment mechanisms, including, but not limited to, a broad hook-and-loop closure in the front of the vest of the present invention that offers a snug fit to the user, especially around the lower back of the user, where other product designs on the market often fail to make good contact with the body.

DETAIL DESCRIPTIONS OF THE INVENTION

Figure 1:
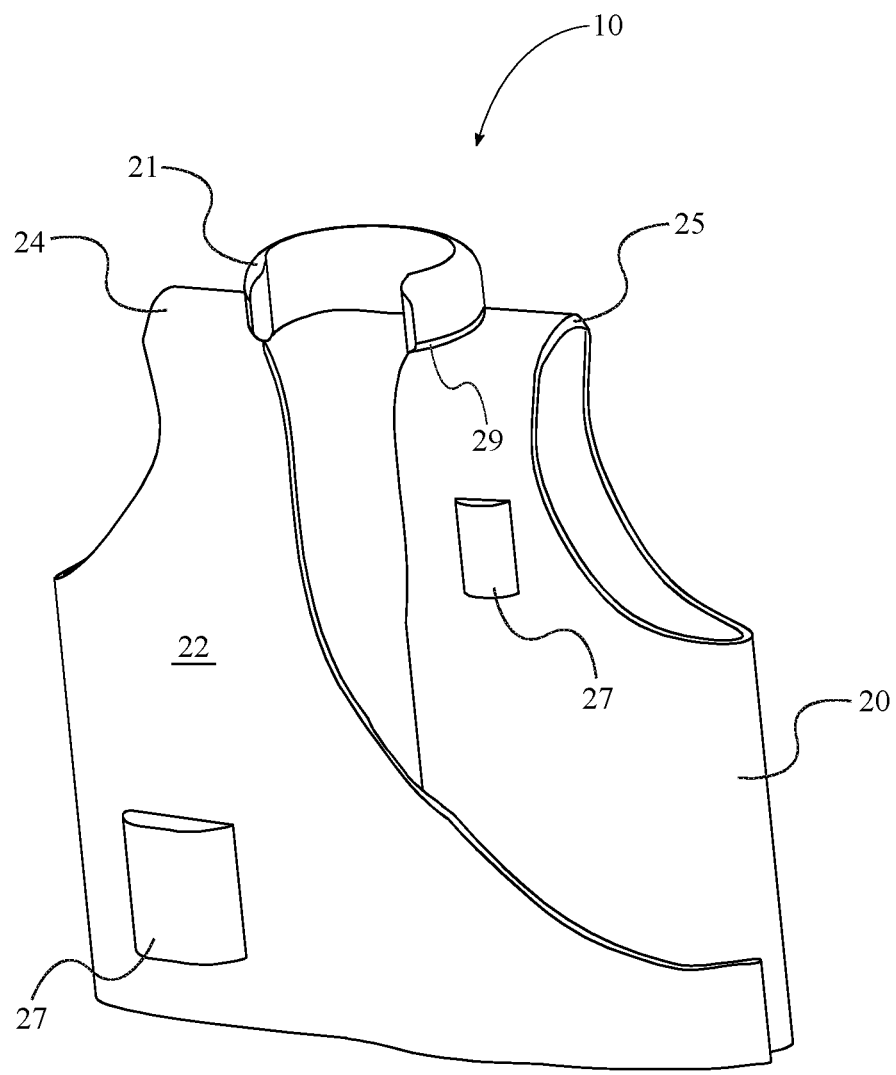
FIG. 1 is perspective view of one embodiment of the present invention.

All illustrations of the drawings are for the purpose of describing selected versions of the present invention and are not intended to limit the scope of the present invention.

The present invention provides a vibrating and heating massage vest that includes a controller and body zones to allow a user to control the massage for desired body parts. The massage vest of the present invention facilitates relief of neck, back, shoulders, etc., of the user through massaging the appropriate body areas of the user and includes a design that promotes good posture while the user is seated. The massage vibrating modules may be configured to vibrate and/or oscillate in various controlled directional and rotational movements, providing a therapeutic massage to the user. The massage vibrating modules may be positioned on the vest for massaging various areas on the back, neck, and shoulders of the user. Additionally, the massage vest includes adjustment mechanisms, including, but not limited to, a broad hook-and-loop closure in the front of the vest of the present invention that offers a snug fit to the user, especially around the lower back of the user, where other product designs on the market often fail to make good contact with the body.

As can be seen in FIG. 1 to FIG. 10, the massage vest 10 of the present invention comprises a vest 20, a plurality of vibrating modules 30, a plurality of heating elements 40, and a controller 70. More specifically, the vest 20 comprises a front 22, and a back 23. The plurality of vibrating modules 30 and the plurality of heating elements 40 are attached to the vest 20 to facilitate convenient and effective massage and heating on the user. The controller 70 is electrically connected to the plurality of vibrators 30 and the plurality of heating elements 40. The controller 70 may be connected via wires to each respective member of the plurality of vibrating modules 30 and the plurality of heating elements for the purpose of control. Further, the controller 70 comprise a power source 71, a processor 79, a display 76, and a body zone diagram 77. The massage vest 10 and the controller 70 of the present invention are powered by the power source 71, which may include, but is not limited to, a battery 81, a car adapter 78, a hardwire power source such as a plug, one or more USB connection ports, at least one of a portable power source such as a rechargeable battery pack that enables the user to be mobile while wearing the present invention. Each of the power sources is selectively connectable to the controller 70 and provides power to the plurality of vibrating modules 30 and the plurality of heating members 40. The processor 79 is electrically connected to the power source 71. The power source 71 can use any of an alternating current (AC) and/or direct current (DC) power source which include batteries, car adaptors, at least one USB (universal serial bus) power plug, etc. With various power supplies that the power source 71 is compatible with, the massage vest 10 provides convenient use of the present invention. The display 76 is electrically connected to the processor 79, and the body zone diagram 77 is displayed on the display 76 through the processor 79. The body zone diagram 77 provides an illustrative body massage diagram that includes areas the plurality of massage modules 30 and the plurality of heating elements 49 are distributed. Additionally, the body zone diagram 77 offers on/off buttons that can be used to control massage of specific body areas so that the user can select and start massaging by simply pushing any of the buttons.

As can be seen in FIG. 1 to FIG. 5 and FIG. 7, the vest 20 of the massage vest 10 can be a vest of any size and shape suitable for the user. The vest 20 can be made of any material, including non-elastic material, suitable for positioning the plurality of vibrating modules 30 and the plurality of heating elements 40. In some embodiments, the vest 20 may include fasteners known in the art, which may be of a hook, button, or Velcro® fastener. In the preferred embodiment of the present invention, the vest 20 comprises a collar 21, a first shoulder 24, a second shoulder 25, a plurality of closure 26, at least one pocket 27, at least one pouch 28, and a bending rod 29. More specifically, the collar 21 is terminally attached to the back 23 and the plurality of vibrating modules 30 is attached to the collar 21. The first shoulder 24 and the second shoulder 25 are positioned on the back 23 adjacent the collar 21 and the plurality of vibrating modules 30 is attached to the first shoulder 24 and the second shoulder 25. In some embodiments, the vest 20 may extend to cover the first shoulder 24 and the second shoulder 24 of the user to provide therapeutic massage to the shoulder areas.

Figure 2:
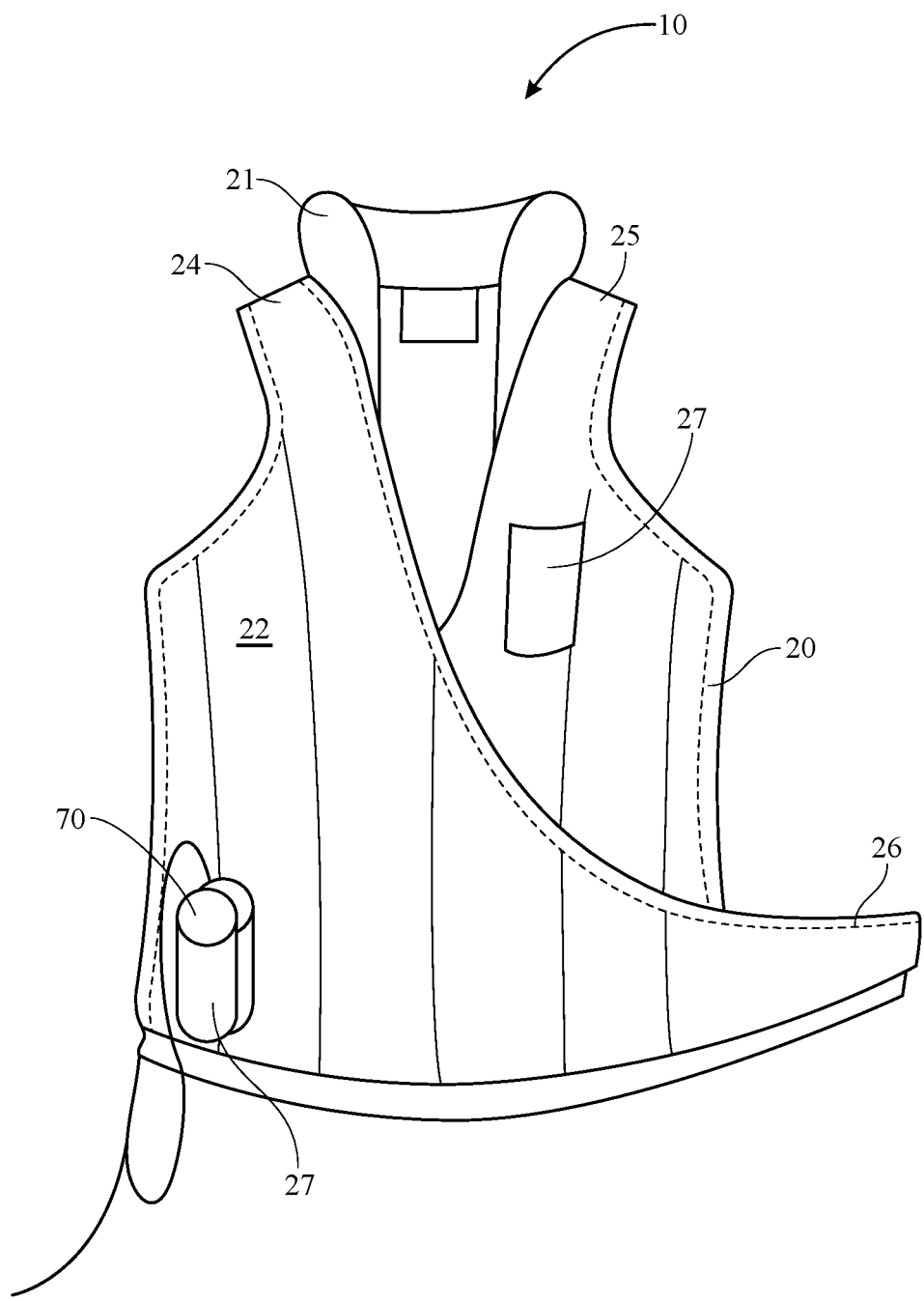
FIG. 2 is a front view of the present invention, wherein a broad hook-and-loop closure is positioned to the front.
Figure 3:
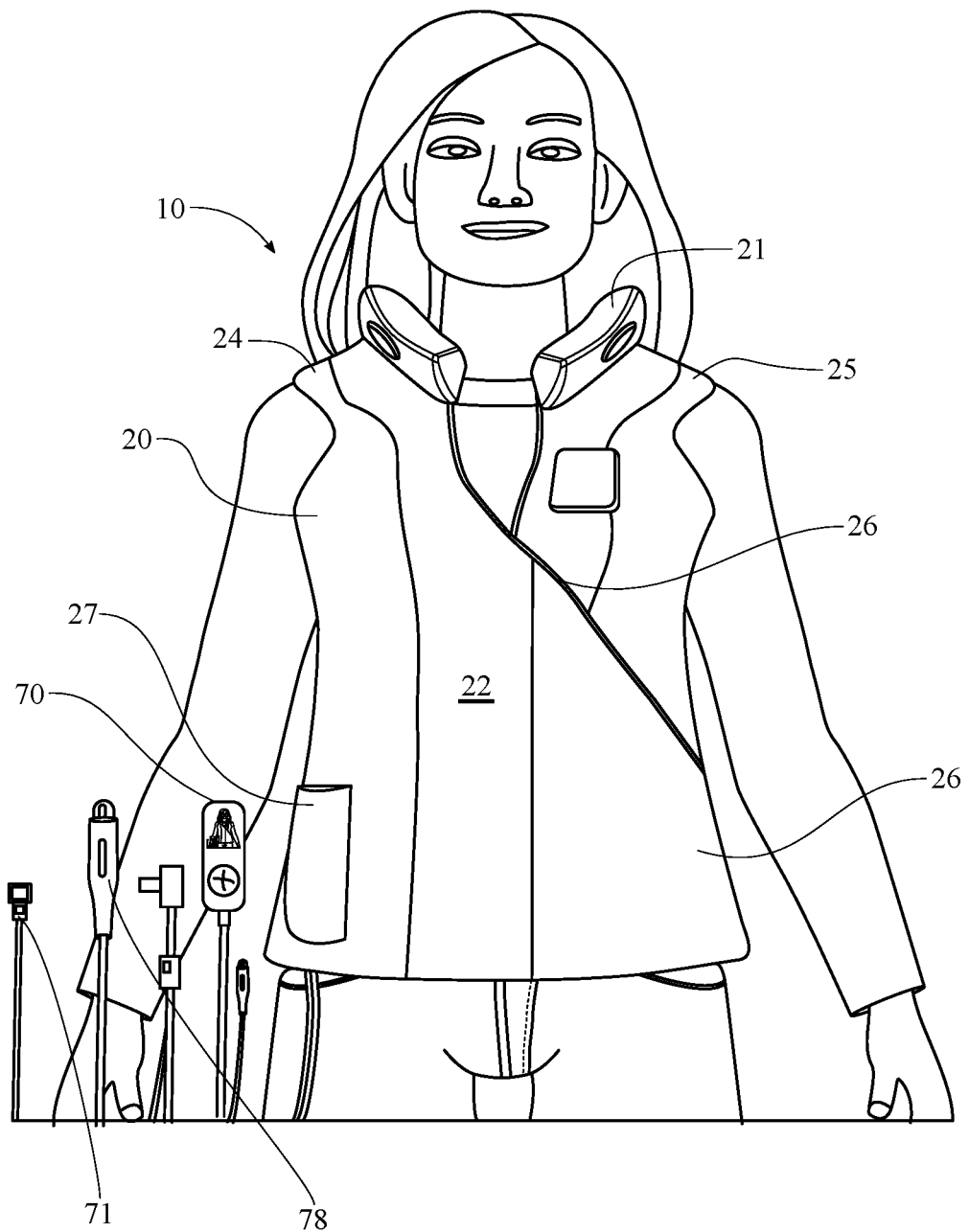
FIG. 3 is a front view of an alternative embodiment of the present invention worn by a user.
Figure 4:
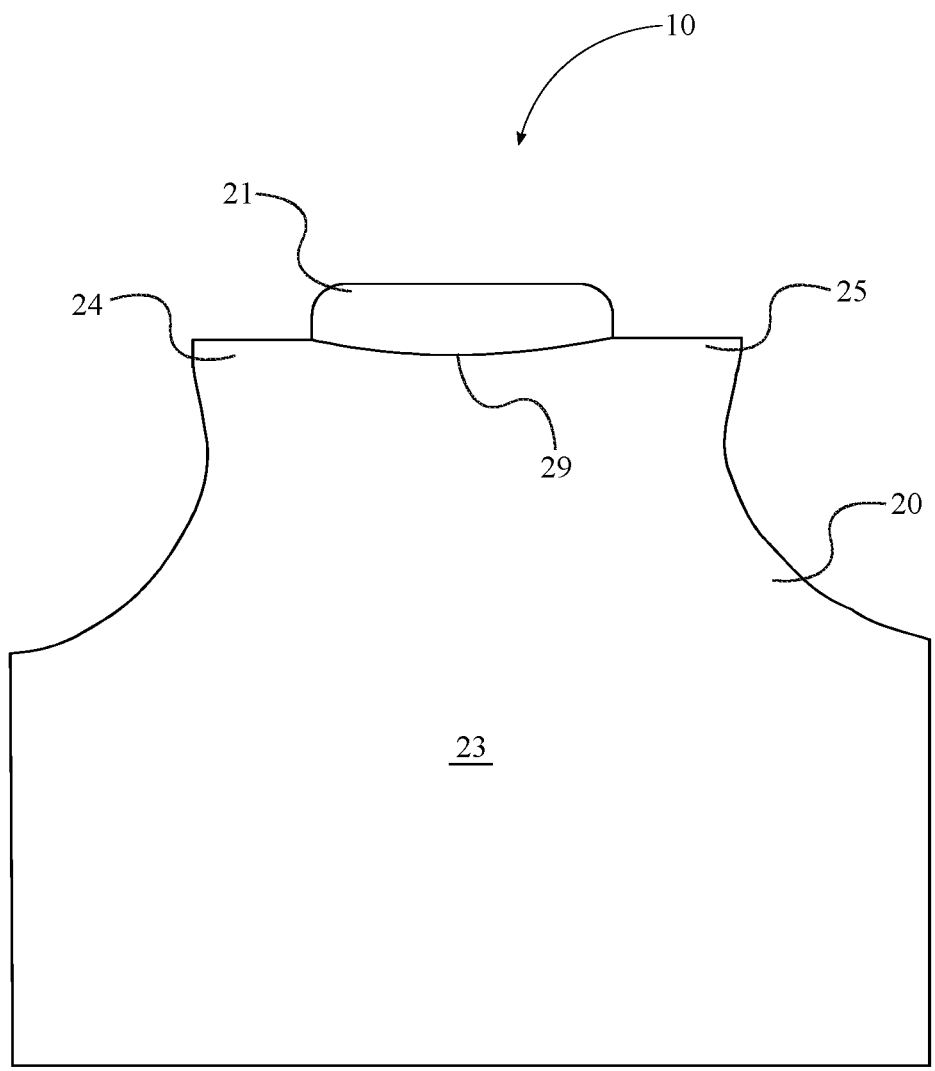
FIG. 4 is a rear view of the present invention.
Figure 5:
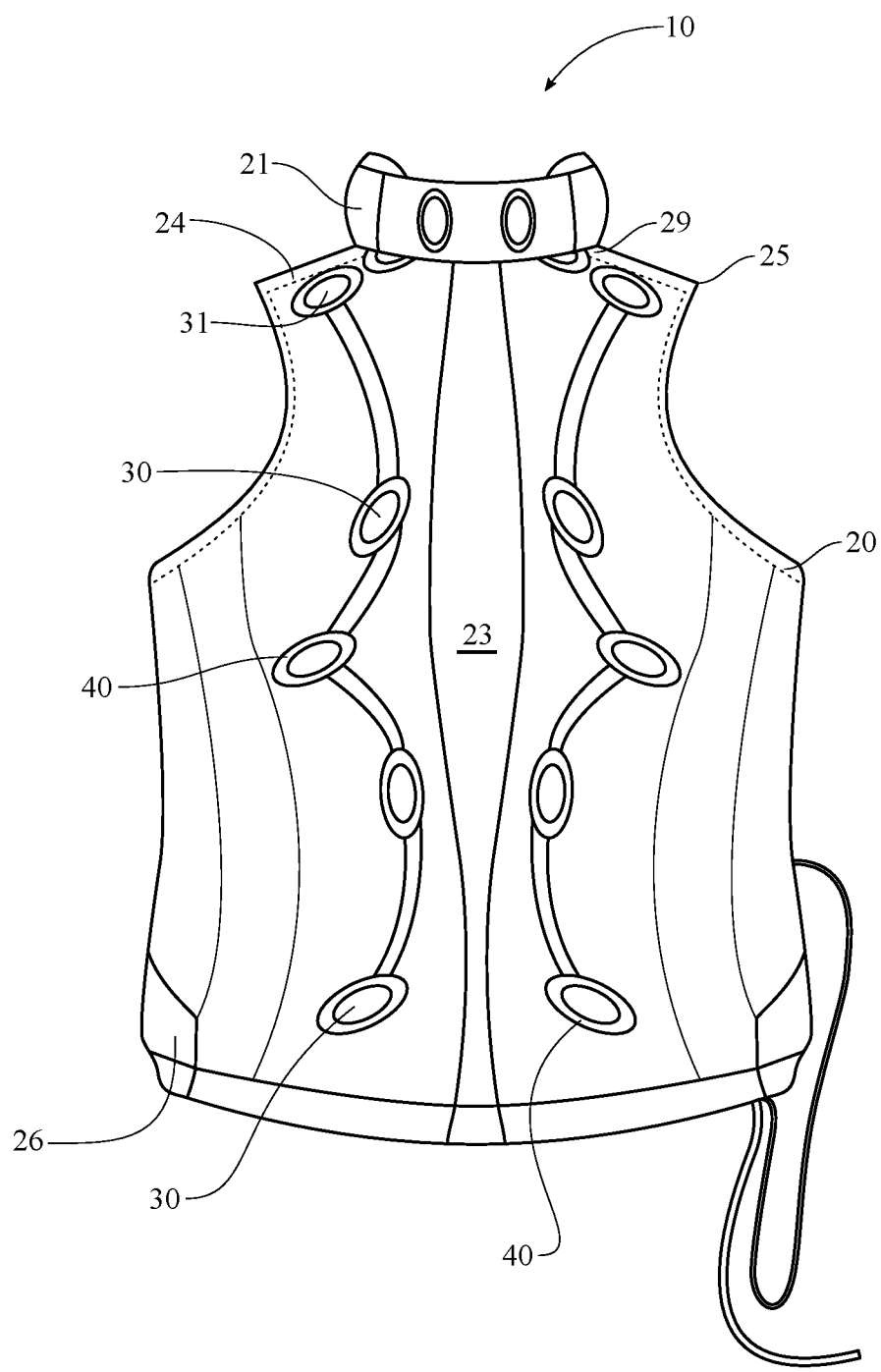
FIG. 5 is a rear view of an alternative embodiment of the present invention, wherein a plurality of vibrating modules and a plurality of heating elements are positioned on the present invention.
Figure 6:
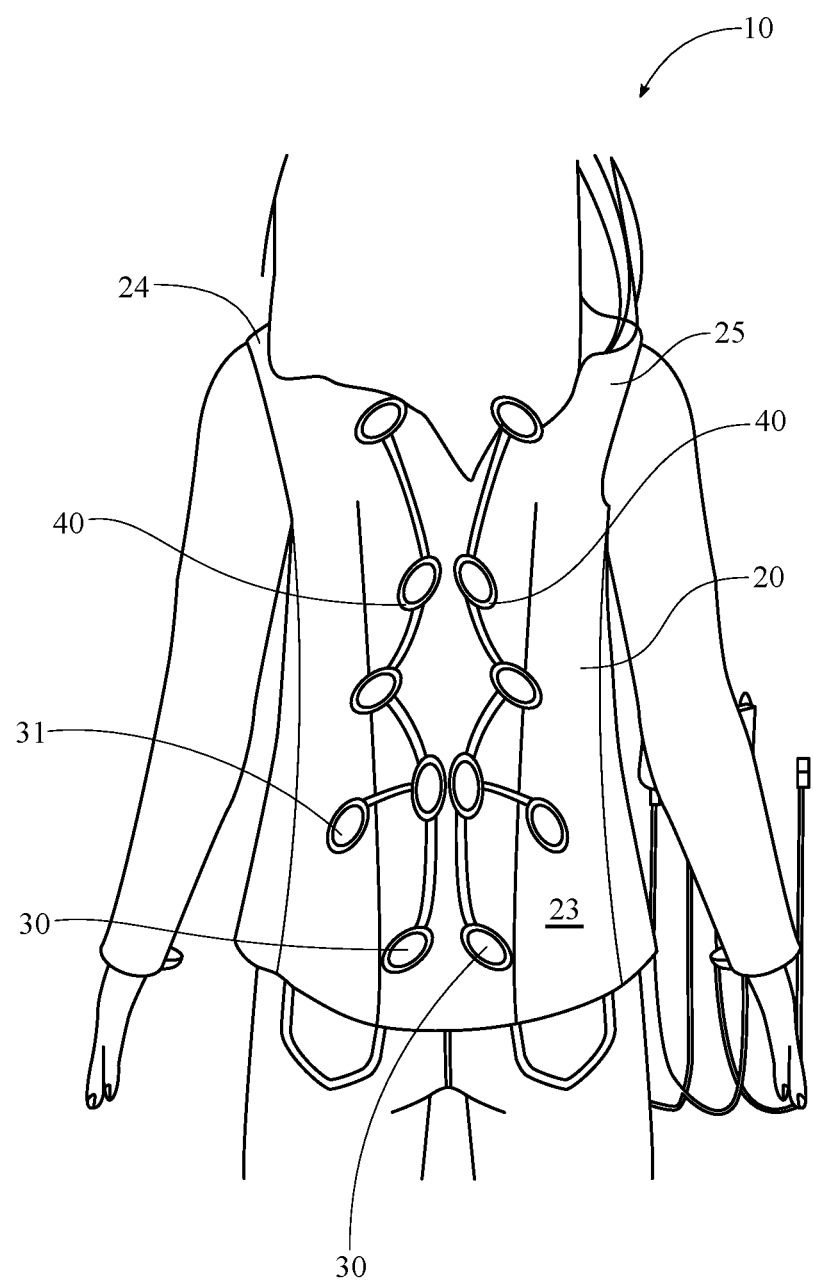
FIG. 6 is a rear view of the alternative embodiment of the present invention worn by the user.

As can be seen in FIG. 1 to FIG. 3, the front of the vest 20 may comprise a first side piece and a second side piece. The first side piece is connected along and adjacent to the back, while the second side piece is connected along and adjacent to the back, opposite to the first side piece. Moreover, the first side piece, the back, and the second side piece are a continuous piece of material. The first side piece is also longer than the second side piece, which allows the first side piece to be laid over and about the second side piece. Furthermore, the first side piece is attached to the second side piece by the plurality of closures.

As can be seen in FIG. 1 to FIG. 3, the plurality of closures 26 is positioned on the vest 20 and is designed to wrap around the body and the neck of the user and fastened at a suitable place on the user's body, including, but not limited to, the front neck area, the lower left side of the user's torso near the waist area, etc. The plurality of closures 26 may be a broad hook-and-loop closure that offers a snug fit, especially around the lower back, where other product designs often fail to make good contact with the user's body.

Figure 7:
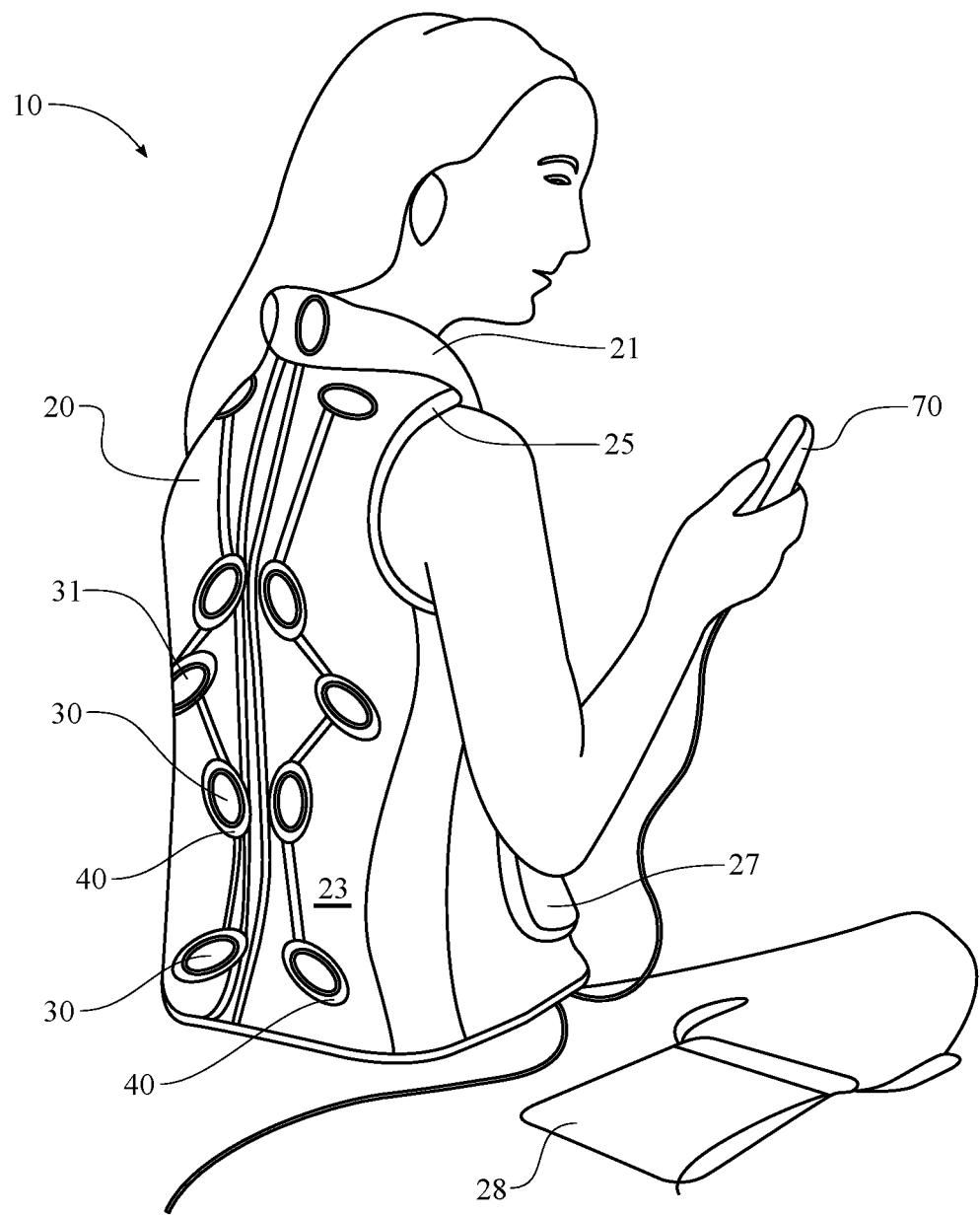
FIG. 7 is a rear view of another embodiment of the present invention worn by a user, wherein a controller and a pouch are included.

In some embodiments, the plurality of pockets and silver linings. In the preferred embodiment, the at least one pocket 27 of the vest 20 may include, but is not limited to, a pocket (chest pocket) placed on the upper left side of the front 22 of the vest 20 and another pocket (hip pocket) placed on the lower right side of the front 22 of the vest 20. In some embodiments, the at least one pocket 27 may be of a size suitable to carry the controller 70, and the chest pocket may be of a suitable size to hold a phone such as a smartphone, a personal computing (PC) device, a tablet, etc. As can be seen in FIG. 7, in some embodiments, the massage vest 10 of the present invention may include at least one pouch 28 that can be designed to store power cables or car travel adapters to make it easy for the user to carry the present invention and use it on the go.

Figure 8:
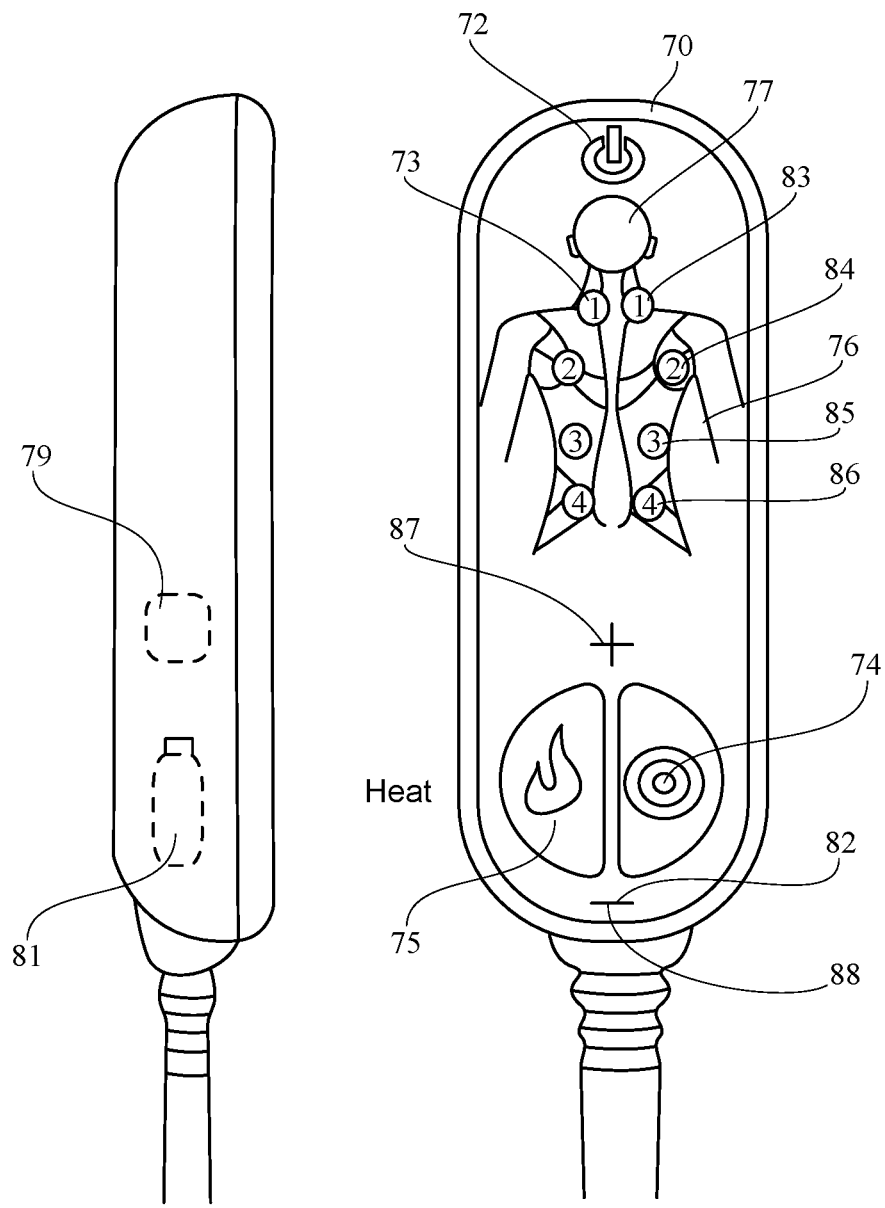
FIG. 8 is an illustration showing the front view and the side view of the controller of the present invention.
Figure 9:
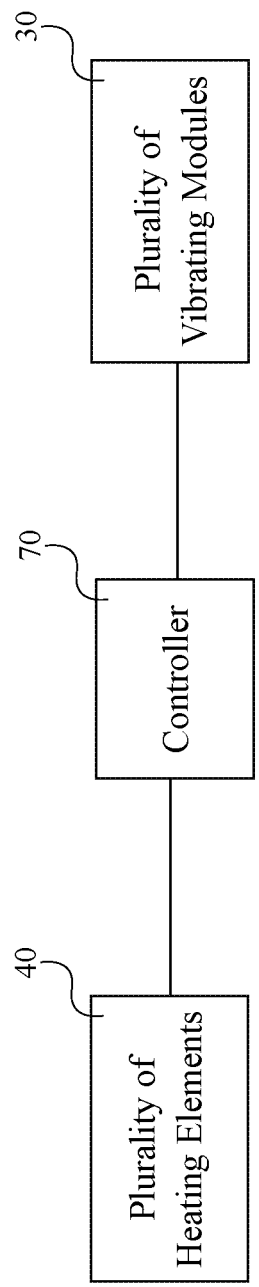
FIG. 9 is an electrical diagram of the present invention, wherein the controller is electrically connected to the plurality of vibrating modules and the plurality of heating elements.
Figure 10:
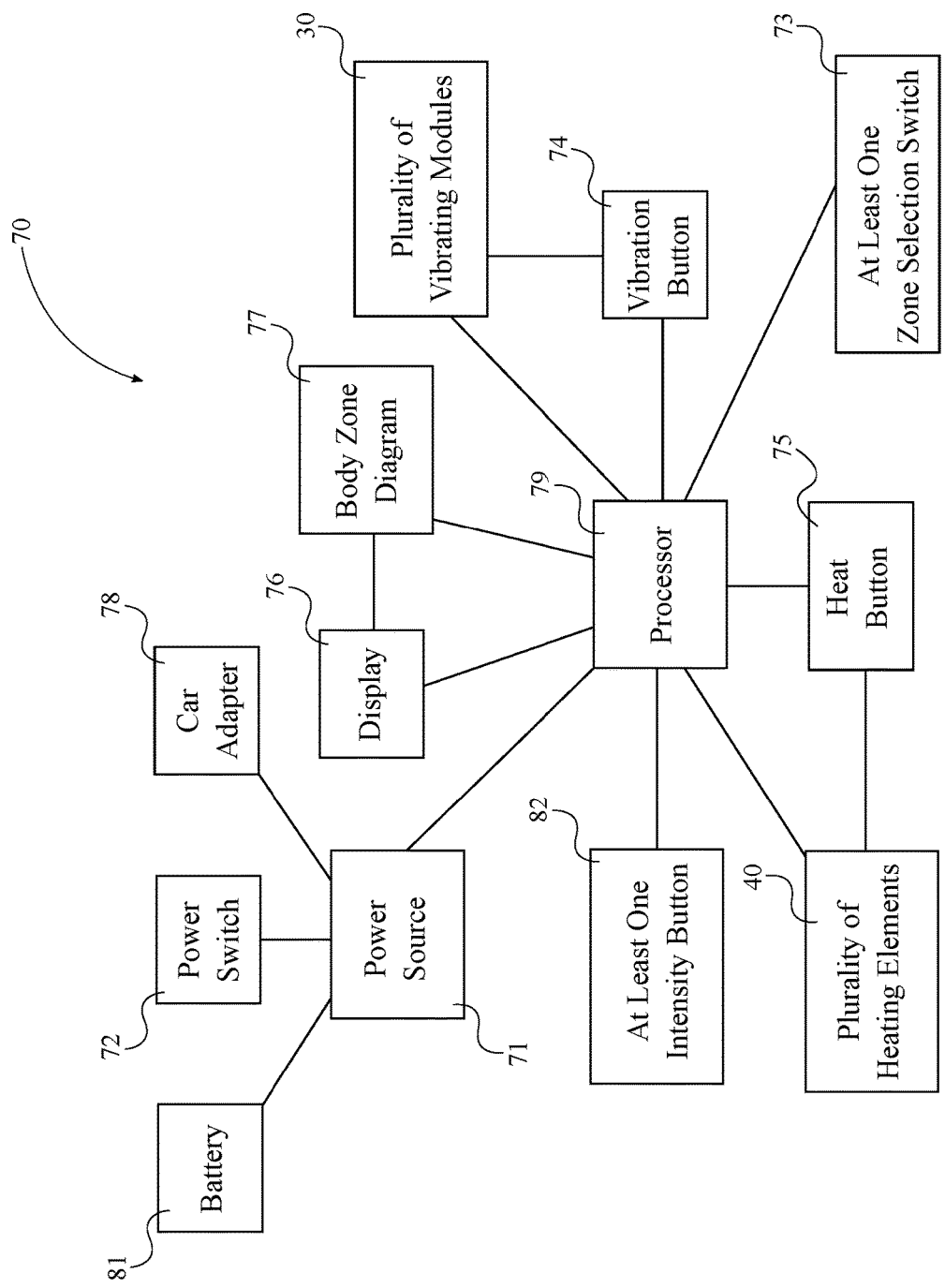
FIG. 10 is an electrical diagram of the present invention, wherein components of the controller are electrically interconnected and are electrically connected to the plurality of vibrating modules and the plurality of heating elements.

As can be seen in FIG. 8 and FIG. 10, the controller 70 of the massage vest 10 comprises at least one zone selection switch 73 that allows the user to selectively control via the controller 70. The at least one zone selection switch 73 is positioned on the body zone diagram 77 and is electrically connected to the processor 79 to enable the user to exactly target the vibrations on the desired locations. The at least one selection switch 73 allows the user to select a desired body zone for massage. The at least one zone selection switch 73 can be configured to allow the user to determine the area to be massaged and/or heated. When the user turns on the at least one selection switch 73, the process 79 activates the corresponding vibrating module of the plurality of the vibrating modules 30 to massage the selected body zone. Additionally, as can be seen in FIG. 8, the at least one zone selection switch 73 comprises a first zone switch 83, a second zone switch 84, a third zone switch 85, and a fourth zone switch 86. More specifically, the first zone switch 83 is positioned on the body zone diagram 77 and corresponding to a neck and shoulder area. The first zone switch 83 is configured to allow the user to select the members of the plurality of vibrating modules 30 and the plurality of heating members 40 positioned adjacent to the neck and shoulders of the user to oscillate and/or vibrate in a desired pattern. The second zone switch 84 is positioned on the body zone diagram 77 and corresponding to a back area below the collar 21 of the vest 20. The third zone switch 85 is positioned on the body zone diagram 77 and corresponding to a middle area of the back 23 of the vest 20, substantially in the middle area of the user's back. Further, the fourth zone switch 86 is positioned on the body zone diagram 77 and corresponding to a lower area of the back 23 of the vest 20. The fourth zone switch 86 is positioned at the bottom of the user's back area. Each of the zones may include a plurality of members of the plurality of vibrating modules 30 and the plurality of heating members 40, of which the user can selectively control the oscillation or vibration, and heating of the area.

As can be seen in FIG. 8 and FIG. 10, the controller 70 comprises a power switch 72, a vibration button 74, a heat button 75, at least one intensity button 82. More specifically, the power switch 72 is electrically connected to the processor 79 and is used to control the electric power to the controller 70 and the vest 20. The vibration button 74 is electrically connected to the plurality of vibrating modules 30 and is electrically connected to the processor 79. The heat button 75 is electrically connected to the plurality of heating elements 40 and is electrically connected to the processor 79 as well. The vibration button 74 and the heat button 75 are used to turn on and off the plurality of vibrating modules 30 and the plurality of heating elements 40, respectively, for selectively controlling the oscillation pattern or the magnitude and frequency of the vibrations and heat levels (the amount of heat generated by heating elements). Additionally, the at least one intensity button 82 is electrically connected to the processor 79. The at least one intensity button 82 may be electrically connected to the plurality of vibrating modules 30 and the plurality of heating elements 40. The at least one intensity button 82 allows the user to increase or decrease the intensity of massage through the plurality of vibrating modules 30 and the heating intensity of the plurality of heating elements 40. Further, the at least one intensity button 82 comprises an increasing intensity button 87 and a decreasing intensity button 88.

As can be seen in FIG. 7, in some embodiments of the present invention, each of the plurality of vibrating modules 30 comprises a vibrator 31. The vibrator 31 is electrically connected to the processor 79 of the controller 70. The vibrator 31 may include, by is not limited to, a motor or massager, which causes each of the plurality of vibrating modules 30 to oscillate or vibrate in a plurality of directions. In some other embodiments, the vibrator 31 may cause the plurality of vibrating modules 30 to pivot about an axis. In some embodiments, the vibrator 31 may selectively cause the plurality of vibrating modules 30 to pivot in various directions, including a horizontal direction, a vertical direction, and a 360-degree rotational pivot direction, providing different styles and types of massage to the user. In some embodiments, the user can selectively control the oscillation or vibration of the plurality of vibrating modules 30 using the controller 70.

As can be seen in FIG. 7, in some embodiments of the present invention, each of the plurality of heating elements 40 is positioned on one of the plurality of vibrating modules 30. The plurality of heating elements 40 may include any suitable heating elements known to those skilled in this art. Further, the plurality of heating elements 40 may be located throughout the entire vest 20 or only in a suitable portion thereof. In some embodiments, the present invention may include a surface embossment that accentuates the massage and heating functions on the targeted massage zones.

Although the invention has been explained in relation to its preferred embodiment, it is to be understood that many other possible modifications and variations can be made without departing from the spirit and scope of the invention as hereinafter claimed.

What is claimed is:

1. A vibrating and heating massage vest comprising:
a vest;
a plurality of vibrating modules;
a plurality of heating elements;
a controller;
a plurality of closures;
the vest comprising a front, a back, a collar, a first shoulder, and a second shoulder;
the controller comprising a power source, a processor, a display, a body zone diagram, and at least one zone selection switch;
the front comprising a first side piece and a second side piece;
the collar being terminally attached to the back;
the first shoulder and the second shoulder being positioned on the back adjacent the collar;
the plurality of vibrating modules being attached to the vest;
the plurality of heating elements being attached to the vest;
the plurality of vibrating modules being distributed across the collar, the first shoulder, the second shoulder, and the back;
each of the plurality of vibrating modules being perimetrically encircled by a corresponding heating element from the plurality of heating elements;
the controller being electrically connected to the plurality of vibrators and the plurality of heating elements;
the processor being electrically connected to the power source;
the display being electrically connected to the processor;
the body zone diagram being displayed on the display through the processor;
the at least one zone selection switch being positioned on the body zone diagram;
the at least one zone selection switch being electrically connected to the processor;
the first side piece being connected along and adjacent to the back;
the second side piece being connected along and adjacent to the back, opposite to the first side piece;
the first side piece, the back, and the second side piece being a continuous piece of material;
the first side piece being longer than the second side piece;
the first side piece being laid over and about the second side piece; and
the first side piece being attached to the second side piece by the plurality of closures.

2. The vibrating and heating massage vest as claimed in claim 1 further comprising:
the at least one zone selection switch comprising a first zone switch; and
the first zone switch being positioned on the body zone diagram corresponding to a neck and shoulder area.

3. The vibrating and heating massage vest as claimed in claim 1 further comprising:
the at least one zone selection switch comprising a second zone switch; and
the second zone switch being positioned on the body zone diagram corresponding to a back area below the collar of the vest.

4. The vibrating and heating massage vest as claimed in claim 1 further comprising:
the at least one zone selection switch comprising a third zone switch; and the third zone switch being positioned on the body zone diagram corresponding to a middle area of the back of the vest.

5. The vibrating and heating massage vest as claimed in claim 1 further comprising:
   the at least one zone selection switch comprising a fourth zone switch; and
   the fourth zone switch being positioned on the body zone diagram corresponding to a lower area of the back of the vest.

6. The vibrating and heating massage vest as claimed in claim 1 further comprising:
   the controller comprising a power switch; and
   the power switch being electrically connected to the processor.

7. The vibrating and heating massage vest as claimed in claim 1 further comprising:
   the controller comprising a vibration button;
   the vibration button being electrically connected to the plurality of vibrating modules; and
   the vibration button being electrically connected to the processor.

8. The vibrating and heating massage vest as claimed in claim 1 further comprising:
   the controller comprising a heat button;
   the heat button being electrically connected to the plurality of heating elements; and
   the heat button being electrically connected to the processor.

9. The vibrating and heating massage vest as claimed in claim 1 further comprising:
   at least one intensity button; and
   the at least one intensity button being electrically connected to the processor.

10. The vibrating and heating massage vest as claimed in claim 9 further comprising:
    the at least one intensity button being electrically connected to the plurality of vibrating modules.

11. The vibrating and heating massage vest as claimed in claim 9 further comprising:
    the at least one intensity button being electrically connected to the plurality of heating elements.

12. The vibrating and heating massage vest as claimed in claim 9 further comprising:
    the at least one intensity button comprising an increasing intensity button.

13. The vibrating and heating massage vest as claimed in claim 9 further comprising:
    the at least one intensity button comprising a decreasing intensity button.

14. The vibrating and heating massage vest as claimed in claim 1 further comprising:
    each of the plurality of vibrating modules comprises a vibrator; and
    the vibrator is electrically connected to the processor of the controller.

15. The vibrating and heating massage vest as claimed in claim 1 further comprising:
    at least one pocket with a silver lining; and
    the at least one pocket with the silver lining being positioned on the vest.

16. The vibrating and heating massage vest as claimed in claim 1 further comprising:
    a pouch; and
    the pouch being located offset from the vest.

17. The vibrating and heating massage vest as claimed in claim 1 further comprising:
    the power source comprising at least one USB (Universal Serial Bus) plug.

18. The vibrating and heating massage vest as claimed in claim 1 further comprising:
    the power source comprising an AC (Alternating Current) power source.

19. The vibrating and heating massage vest as claimed in claim 1 further comprising:
    the power source comprising a DC (Direct Current) power source.

* * * * *